Figure 1:
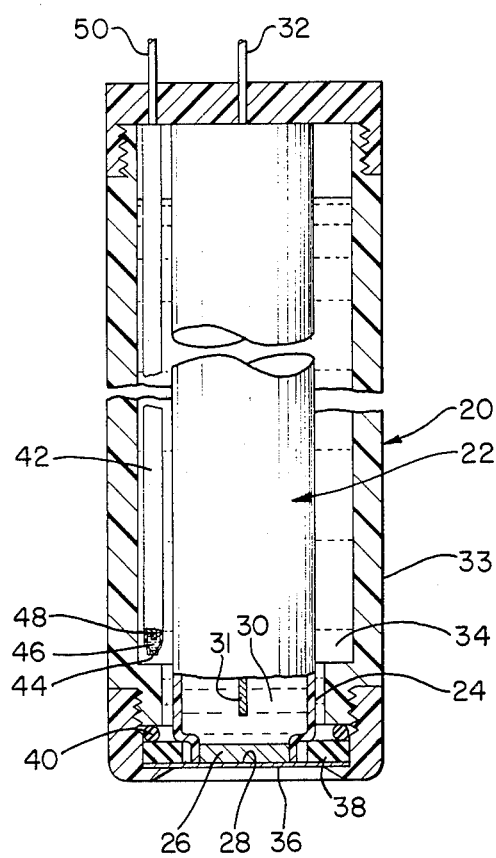

United States Patent [19]

Frant et al.

[11] 3,950,231

[45] Apr. 13, 1976

[54] METHOD OF DETERMINING HYDROGEN CYANIDE

[75] Inventors: Martin S. Frant, Newton; John H. Riseman; John A. Krueger, both of Cambridge, all of Mass.

[73] Assignee: Orion Research Incorporated, Cambridge, Mass.

[22] Filed: Aug. 30, 1974

[21] Appl. No.: 502,171

Related U.S. Application Data

[62] Division of Ser. No. 349,224, April 9, 1973, Pat. No. 3,859,191.

[52] U.S. Cl. ............................................. 204/1 R
[51] Int. Cl.² ........................................ G01N 27/46
[58] Field of Search......... 204/1 T, 195 P, 1 N, 1 K; 324/29

[56] References Cited
UNITED STATES PATENTS

| | | | |
|---|---|---|---|
| 2,864,747 | 12/1958 | Roth | 204/1 T |
| 2,912,367 | 11/1959 | Asendorf et al. | 204/1 T |

Primary Examiner—G. L. Kaplan
Attorney, Agent, or Firm—Schiller & Pandiscio

[57] ABSTRACT

An improved gas-sensing electrochemical cell for measuring hydrogen cyanide gas in a sample solution. The cell comprises a potentiometric silver ion-sensitive electrode and a reference electrode, both in contact with an internal standard solution comprising an aqueous solution of an argento cyanide complex. A hydrophobic hydrogen cyanide gas-permeable membrane separates the sample solution from the internal solution.

11 Claims, 2 Drawing Figures

METHOD OF DETERMINING HYDROGEN CYANIDE

This is a division of U.S. Pat. application Ser. No. 349,244, filed April 9, 1973 and issued as U.S. Pat. No. 3,859,191 on Jan. 7, 1975.

This invention relates to electrochemical analysis and particularly to analytical devices in which the hydrogen cyanide content of a sample gas in a liquid is measured by potentiometrically monitoring the hydrogen cyanide activity. electrolyte Hydrogen cyanide in solution is known to be highly toxic yet it is widely used commercially in the manufacturing of dyes and plastics, and as a fumigant in the citrus industry. Additionally, many cyanide salts in acid solution such as plating baths will decompose to release free HCN. It is therefore quite important that one be able to measure the hydrogen cyanide activity as distinct from the cyanide ion activity in a sample solution.

It is known that one can measure the concentration of a gas (such as ammonia) dissolved in aqueous solution, by diffusing the ammonia from the sample liquid through a membrane, which is selectively permeable to ammonia gas, into an electrolyte. The electrolyte has immersed therein a pH electrode and a reference electrode so that a galvanic cell is formed in which the potential developed is related by the well-known Nernst equation to the hydrogen ion activity in the cell. This latter activity is proportional to the logarithm of the partial pressure of the ammonia gas dissolved in the sample. It will be seen that the potential developed by the system is an indirect measure of the ammonia gas activity or concentration.

It is also known that a similar electrochemical system can be used to detect the presence of carbon dioxide. In such a system a pH glass electrode and a reference electrode are immersed in a bicarbonate solution which is separated from the sample medium by a membrane permeable to carbon dioxide. Again, the potential developed across the two electrodes is an indirect measure of the partial pressure of the carbon dioxide in the sample medium.

A principal object of the present invention is to provide an improved electrochemical cell for measuring the hydrogen cyanide content of samples. Other objects of the present invention are to provide a hydrogen cyanide sensor which rapidly and accurately measures the activity of hydrogen cyanide in a sample medium; and to provide such a sensor capable of measuring very low levels (e.g. $1 \times 10^{-7}M$) of hydrogen cyanide.

Generally, the hydrogen cyanide sensor of the present invention is an electrochemical cell of the general type described above.

However, a pH electrode is not responsive to cyanide ions; known cyanide sensors (such as electrodes having an AgI membrane) in such gas detecting systems or cells are not particularly useful because the latter type of sensor operates on the basis of dissolution or thermodynamically irreversible reaction of the cell membrane with excess $CN^-$, and the reaction products will inevitably pollute the internal reference solution of the cell.

The silver sensing electrode employed in the present invention as the cyanide ion-sensing element is substantially that described in U.S. Pat. No. 3,672,962 issued June 27, 1972 to M. S. Frant and J. W. Ross.

Such a silver-sensing electrode is characterized in that the ion-sensitive portion thereof is essentially a dense, imporous pellet or membrane of substantially pure $Ag_2S$, at least the surface of which is intended to contact the solution having silver ions being free from any metal, particularly silver. Such silver electrodes, which are commercially available from Orion Research Incorporated, Cambridge, Massachusetts, exhibit a substantially Nernstian response to the activity of silver ions in solution.

In an alternative embodiment as will be described, the cyanide ion-sensing element is a cadmium ion responsive electrode substantially as described in U.S. Pat. No. 3,591,464 issued July 6, 1971 to M. S. Frant and J. W. Ross. Such a cadmium sensitive electrode is characterized in that the ion-sensitive portion thereof is a solid substantially imporous pellet or membrane formed of a mixture of $Ag_2S$ and $CdS$. Such cadmium electrodes also available commercially from Orion Research Incorporated, exhibit a substantially Nernstian response (divalent) to the activity of cadmium ions in solution.

Figure 2:
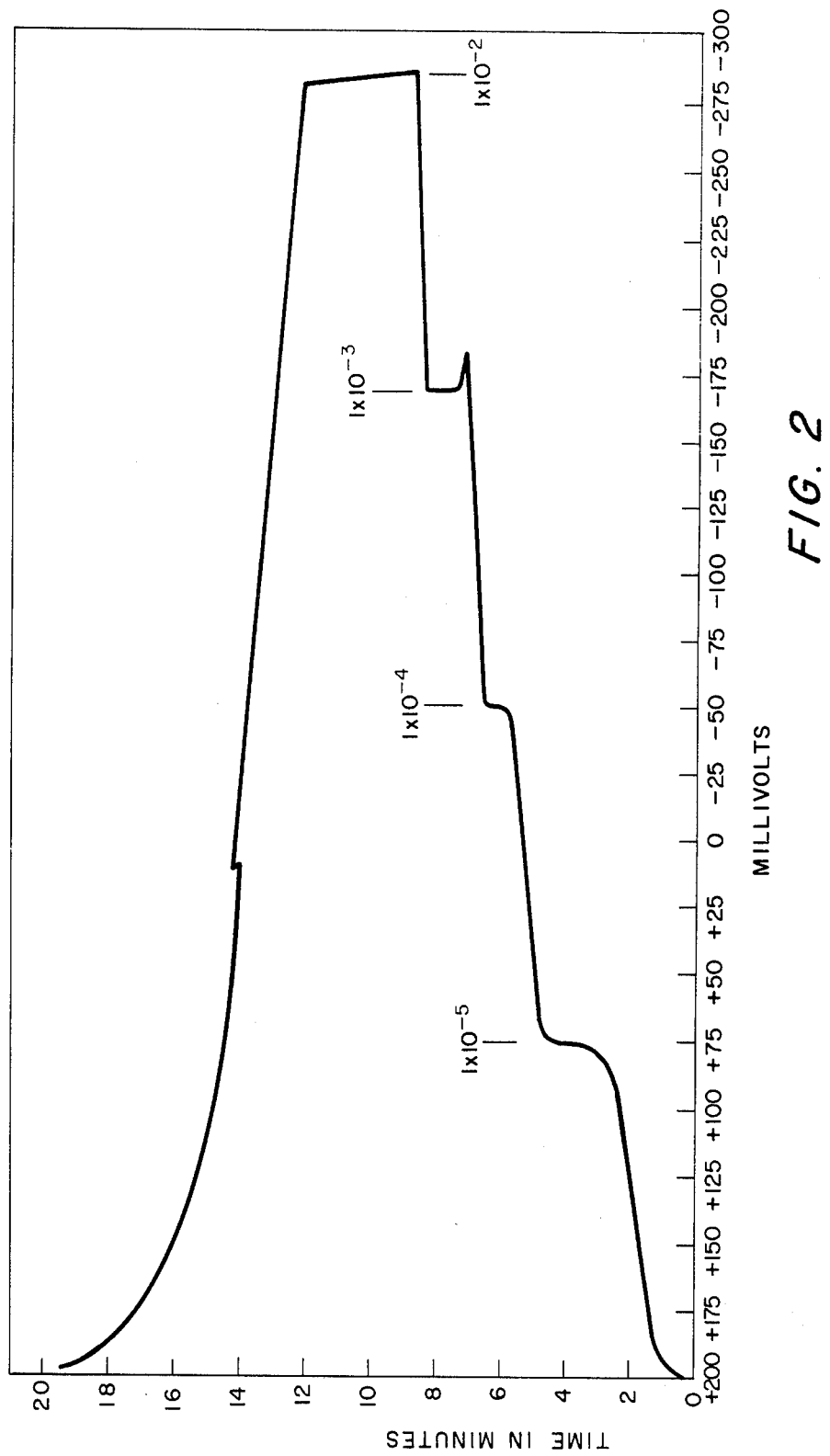

Other objects of the invention will in part be obvious and will in part appear hereinafter. The invention accordingly comprises the apparatus possessing the construction and arrangement of elements, and the process including the several steps and relation of one or more of such steps with respect to the other, all of which are exemplified in the following detailed disclosure and the scope of the application of which will be indicated in the claims. For a fuller understanding of the nature and objects of the present invention, reference should be had to the following detailed description taken in connection with the accompanying drawings wherein:

FIG. 1 is an idealized cross-section taken through a hydrogen cyanide sensor embodying the principles of the present invention; and FIG. 2 is a graph indicating the response in millivolts of a hydrogen cyanide cell to various concentrations of hydrogen cyanide in different sample media.

The electrochemical cell of the present invention as shown in FIG. 1 generally at 20 and includes a first or silver electrode assembly 22 which is the well known silver ion-sensitive electrode comprising case 24, one end of which is capped or closed with pellet 26 of substantially pure $Ag_2S$ preferably ground to form a plane outer surface 28. The interior of silver electrode assembly 22 is filled with a reference solution 30, typically an aqueous saturated solution of AgCl and KCl, and a reference electrode 31, usually of Ag/AgCl is immersed therein. The reference electrode is connected to an external lead 32. Silver electrode 22 is disposed within hollow enclosure 33 which is made of a substantially chemically inert, electrically insulating material such as epoxy, polytetrafluorethylene or the like.

In contact with the silver sensing portion of the silver electrode and disposed within enclosure 38 is a body of electrolyte 34 which will be described in detail hereafter.

Membrane 36, which is permeable to HCN gas, is supported about its periphery by one side of spacer ring 38. The latter is sealed across an opening into enclosure 33 by elastomeric O-Ring 40. Spacer ring 38 and O-Ring 40 are so dimensioned that membrane 36 is immediately adjacent the planar surface 28 of the $Ag_2S$ pellet 26 so that the interspace between surface 28 and membrane 36 contains an extremely thin film, preferably less than a mil inch, of electrolyte 34.

Membrane 36 is formed of a microporous hydrophobic material which is sufficiently porous or gas permeable such that HCN gas will readily diffuse therethrough, but the membrane will not permit any passage of liquids or ionic constituents dissolved in the liquids. Additionally, of course, the membranes should be substantially inert with respect to the chemical constituents with which it is intended to come in contact and particularly with respect to hydrogen cyanide. The membrane additionally should be made of a substantially insulating electrical material. To this end, suitable membranes can be formed of polytetrafluorethylene, polyvinylchloride, polypropylene and similar materials. A typical such membrane formed of polytetrafluorethylene has an average pore size of 0.5–0.6 microns, an average free area of as much as 80% or more and is typically about 5 mil inches thick.

It will be appreciated that while any of a large number of the standard reference electrodes, such as Ag-/AgCl, can be used to provide the other half cell complementing the silver sulfide electrode in the electrochemical cell of the invention, silver based reference systems will tend to drift, if cyanide ions which are formed in electrolye 34 by diffusion of HCN thereinto actually reach the reference element. This is also true of other reference systems which are attacked by or which will provide changing contact potentials with respect to cyanide ions.

Consequently, the preferred embodiment of the present invention uses as a reference electrode 42 disposed in enclosure 33 and also contracting electrolyte 34, a fluoride ion-sensitive electrode of the type described in U.S. Pat. NO. 3,431,182 issued Mar. 4, 1969 to M. S. Frant, or a pH glass-type electrode or a sodium sensitive glass type electrode. The latter two glass electrodes, while relatively insensitive to the presence of cyanide ion and certainly not attacked by cyanide ion, require that the pH be extremely carefully controlled. Hence it is preferred that the fluoride electrode be used. As is well known, the sensitive element in the latter is a lanthanum fluoride crystalline membrane or pellet 44 which shows no interference when exposed to solutions containing cyanide ions or HCN. The internal electrolyte 46 of electrode 42 is typically an aqueous solution saturated with respect to AgCl and KCl and $10^{-3}$M in fluoride. In contact with electrolyte 46 is the usual Ag/AgCl reference electrode 48 which is connected to external lead 50.

Consequently, the internal electrolyte 34 of the cell of the invention is an aqueous solution in which a fixed level of fluoride ion is provided by the dissociation of a readily soluble fluoride salt such as NaF, KF or the like where the reference electrode 42 is a fluoride-sensitive electrode. The use of a pH or pNa type electrode as reference electrode 42 would of course require a change in the constituency of electrolyte 34 to include the appropriate ion. In addition, it is preferred that electrolyte 34 contain a pH buffer, typically a boric acid at 0.1M, so that the pH is not permitted to change readily. It is preferred that the pH of electrolyte 34 be maintained in the range of between about pH 7 to pH 11, being preferred at around pH 8.5.

Lastly, but very importantly, electrolyte 34 preferably contains a water soluble cyanide complex of the metal to the ion of which electrode 22 is sensitive or responsive, i.e. here a silver cyanide complex. The ion of the complex is desirably present in a concentration greater than $1 \times 10^{-8}$M.

The operation of the HCN sensing electrochemical cell of the present invention is based upon potentiometric measurement of the change in cyanide ion activity in the thin film of electrolyte 34 between surface 28 and membrane 36 caused by diffusion of the hydrogen cyanide through membrane 36. The metal cyanide complex, typically KAg(CN)$_2$, in electrolyte 34 will ionize reversibly as follows to produce a complex ion:

1. $KAg(CN)_2 \rightleftharpoons K^+ + Ag(CN)_2^-$

The complex ion in turn will also ionize reversibly as follows releasing free cyanide ions:

2. $Ag(CN)_2^- \rightleftharpoons Ag^+ + 2CN^-$

Hydrogen cyanide will diffuse into electrolyte 34 until the partial pressure of the hydrogen on both sides of the membrane is equalized, and will dissolve in electrolyte 34 providing same additional cyanide ions. The presence of these additional free cyanide ions tends to dipress the activity of the free silver ions, thereby changing the potential at electrode 22 because of the relationship 3. $A_{Ag} \sim 1/A_{CN}$ where $A_{Ag}$ and $A_{CN}$ are respectively the activities of the free silver and cyanide ions in solution.

If no soluble metal silver complex is dissolved in electrolyte 34 there will nonetheless be a minute amount of silver ions present in the electrolyte because of the small but finite solubility of the Ag$_2$S of pellet 26 in water. Because the silver electrode is capable of measuring extremely low (ca $10^{-30}$M) concentrations of silver, the cell will thus function as a CN$^-$ detector but the very low level of silver ion concentration tends to make the cell drifty and somewhat unreliable. By establishing a higher silver level with the cyanide complex, stable cell operation is achieved.

It will be apparent that the slope of the electrochemical cell will be a typical Nernstain slope and in fact this is what occurs inasmuch as changes in the electrochemical potential developed by the entire cell are dependent solely upon the cyanide concentration in electrolyte 34 detected by silver electrode 22.

In operation of the system, one may operate in either of two basic modes. In the first mode, one can directly measure the partial vapor pressure of free HCN simply by placing the outside of membrane 36 against the sample solution in question and permitting the free hydrogen cyanide in the sample solution to diffuse across the membrane until the partial pressure on both sides of the latter is substantially the same. At that point an equilibrium will be reached and the potential developed by the cell of the present invention will be indicative of the free HCN content of the sample.

In the second mode, one can measure total cyanide. In order to do so, the sample solution is acidified to convert all cyanide ions to hydrogen cyanide. This can be done by adjusting the pH of the sample solution to below 7. In either mode, it is preferred to adjust the osmolality and temperature of the sample solution to match that of electrolyte 34, particularly to minimize transport of water vapor through membrane 36.

An illustrative method of the use of the cell will now be described.

An electrochemical cell according to the invention was made using a silver sensitive electrode (Orion Research Incorporated Model 94–16) as the primary electrode and a fluoride sensitive electrode (Orion Research Incorporated Model 94—09) as a reference electrode. The internal reference solution of the cell was an aqueous solution of $1 \times 10^{-4}M$ NaF, $1 \times 10^{-1}M$ boric acid and $5 \times 10^{-6}$ M $KAg(CN)_2$ all at a pH of 8.5. The cell membrane was a polytetrafluorethylene porous sheet as heretofore described. Each of output leads 32 and 50 respectively from the silver and from the fluoride electrode are connected as respective inputs across a suitable high impedence potentiometric measuring device such as a standard pH meter.

The sample solution was prepared by first providing an aqueous solution of $1 \times 10^{-2}NaH_2PO_4$ adjusted to a pH of 6.86. The cell was immersed in 100 ml. of this sample solution with the membrane contacting the latter. One ml. of an aqueous solution of $1 \times 10^{-3}M$ NaCN was added to the sample solution and the cell potential read. Subsequent additives of appropriate amounts of NaCN solutions, each differing by a decade in molarity were made at spaced intervals. A strip chart (voltage-time) of the response of the cell to each addition is shown in FIG. 2. The various potential levels reached in the strip chart are each identified by the molarity of the free HCN in the corresponding sample solution.

As heretofore noted, an electrode sensitive to cadmium ions can be used in place of the silver ion-sensitive electrode with the silver cyanide complex being replaced by a comparable soluble cadmium cyanide complex. The results will be substantially the same in measuring $CN^-$ for corresponding reasons, although the $Cd^=$ sensitive electrode should not be expected to measure as low a level of cyanide as the $Ag^+$ sensitive electrode can.

Since certain changes may be made in the above apparatus without departing from the scope of the invention herein involved, it is intended that all matter contained in the above description or shown in the accompanying drawing shall be interpreted in an illustrative and not in a limiting sense.

What is claimed is:

1. Method of determining the hydrogen cyanide content of a sample solution comprising the steps of;
   diffusing said hydrogen cyanide into an electrolyte through a membrane which is permeable to said hydrogen cyanide but substantially impermeable to liquids and ionic constituents thereof, and
   measuring the cyanide ion activity in said electrolyte with a potentiometric ion selective electrode.

2. Method as defined in claim 1 wherein said diffusing step includes the steps of:
   placing said membrane between said sample solution and said electrolyte, and allowing the free hydrogen cyanide in said sample solution to diffuse across said membrane so that the partial pressures of said hydrogen cyanide on both sides of said membrane are substantially in equilibrium.

3. Method as defined in claim 1 including the step of adjusting the pH of said electrolyte in the range between pH 7 and pH 11.

4. Method as defined in claim 1, including the step of adjusting the pH of said electrolyte to substantially ground pH 8.5.

5. Method as defined in claim 1 wherein said diffusing step includes the step of acidifying said sample solution to convert all cyanide ions contained therein to hydrogen cyanide.

6. Method as defined in claim 5, including the step of adjusting the osmolality and temperature of said sample solution to match the osmolality and temperature of said electrolyte.

7. Method as defined in claim 1, including the step of adding a pH buffer to said electrolyte.

8. Method as defined in claim 7, wherein the buffer added is boric acid.

9. Method as defined in claim 1, including the step of adding water soluble cyanide complex of silver or cadmium to said electrolyte.

10. Method as defined in claim 1, wherein said step of measuring the cyanide ion activity in said electrolyte includes the steps of contacting said electrolyte with a potentiometric ion-selective electrode which is responsive to the activity of silver ions or cadmium ions in said electrolyte contacting said electrolyte with a reference electrode for providing a potential which is substantially independent of the presence of cyanide ions and measuring the potential difference between said electrodes.

11. Method of determining the hydrogen cyanide content of a sample solution comprising the steps of;
    diffusing said hydrogen cyanide into an electrolyte, having ions of a soluble cyanide complex of a metal, through a membrane which is permeable to said hydrogen cyanide but substantially impermeable to liquids and ionic constituents thereof, and measuring the cyanide ion activity in said electrolyte with a potentiometric ion selective electrode responsive to the cyanide complex of the metal.

* * * * *